United States Patent
Weers et al.

(10) Patent No.: US 10,570,344 B2
(45) Date of Patent: *Feb. 25, 2020

(54) CHEMICAL PROCESS FOR SULFUR REDUCTION OF HYDROCARBONS

(71) Applicant: Baker Hughes, a GE company, LLC, Houston, TX (US)

(72) Inventors: Jerry J. Weers, Richmond, TX (US); Timothy J. O'Brien, Sugar Land, TX (US); Waynn C. Morgan, Alvin, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 81 days.

This patent is subject to a terminal disclaimer.

(21) Appl. No.: 15/799,704

(22) Filed: Oct. 31, 2017

(65) Prior Publication Data

US 2018/0051217 A1 Feb. 22, 2018

Related U.S. Application Data

(63) Continuation-in-part of application No. 15/470,196, filed on Mar. 27, 2017.

(60) Provisional application No. 62/323,120, filed on Apr. 15, 2016.

(51) Int. Cl.
| | | |
|---|---|---|
| *C10G 29/20* | (2006.01) | |
| *C07C 7/11* | (2006.01) | |
| *C10G 53/04* | (2006.01) | |
| *C10G 29/02* | (2006.01) | |

(52) U.S. Cl.
CPC ............ *C10G 29/20* (2013.01); *C10G 29/02* (2013.01); *C10G 2300/202* (2013.01); *C10G 2300/44* (2013.01); *C10G 2400/02* (2013.01); *C10G 2400/04* (2013.01)

(58) Field of Classification Search
None
See application file for complete search history.

(56) References Cited

U.S. PATENT DOCUMENTS

| | | | |
|---|---|---|---|
| 2,152,722 | A | 4/1939 | Yabroff et al. |
| 2,156,577 | A | 5/1939 | Yabroff et al. |
| 2,164,851 | A | 7/1939 | Yabroff et al. |
| 2,315,766 | A | 4/1943 | Border |
| 5,308,553 | A | 5/1994 | Cisneros |
| 5,582,714 | A | 12/1996 | Forte |
| 5,582,808 | A | 12/1996 | Patek |
| 5,753,102 | A | 5/1998 | Funakoshi et al. |
| 5,910,440 | A | 6/1999 | Grossman et al. |
| 6,267,938 | B1 | 7/2001 | Warrender et al. |
| 6,808,621 | B1 | 10/2004 | Cisneros |
| 7,198,761 | B2 | 4/2007 | Buelow et al. |
| 7,326,822 | B1 | 2/2008 | Cisneros |
| 8,133,288 | B2 | 3/2012 | Lumsden et al. |
| 8,992,769 | B2 | 3/2015 | O'Rear et al. |
| 2003/0042172 | A1* | 3/2003 | Sharivker ............. C10G 15/08 208/108 |
| 2017/0028346 | A1 | 2/2017 | Mo et al. |

FOREIGN PATENT DOCUMENTS

| | | | |
|---|---|---|---|
| CN | 103602348 A | | 2/2014 |
| CN | 103242897 B | * | 4/2015 |

OTHER PUBLICATIONS

Stahl, C.R., et al., "Determination of Organic Disulfides by Reduction with Sodium Borohydride", Analytical Chemistry, Jan. 1957, vol. 29, No. 1, 154-155.
Borane Reagents, www.organic-chemistry.org/chemicals/reductions/boranes.shtm, Feb. 25, 2016, 1-4.
HGR P FOR Mercury Removal, Calgon Carbon Corporation Product Bulletin, 2015, 1 page.
CPG LF 12×40 Acid Washed Granular Activated Carbon, Calgon Carbon Corporation, 2007, 2 pages.
CPG LF 12×40 Acid Washed Granular Activated Carbon, Calgon Carbon Corporation Data Sheet, 2015, 2 pages.
BG-HHM Powdered Activated Carbon, Calgon Carbon Corporation Data Sheet, 2015, 1 page.
Huang, Huan, et al., "Effect of valence of copper on adsorption of dimethyl sulfide from liquid hydrocarbon streams on activated bentonite", Chemical Papers, 2014, 68(1), 98-104.
DMS Dimethyl Sulfide Overview, Bulletin # 200B, Gaylord Chemical Company, LLC, Oct. 2007, 1-12.
King, David L., "Removal of Sulfur Components from Low Sulfur Gasoline Using Copper Exchange Zeolite Y at Ambient Temperature", Pacific Northwest National Laboratory, Richmond, WA, date unknown, 1 page.
Shen, Yafie, et al., "Novel Desulfurization Method of Sodium Borohydride Reduction for Coal Water Slurry", Energy Fuels, 2011, 25, 2963-2967.
Shurong, Gao, et al., "Desulfurization of fuel oils: Mutual solubility of ionic liquids and fuel oil", Fuel 173, 2016, 164-171.
Lee, Jieun, et al., "Adsorptive Removal of Dimethyl Disulfide in Olefin Rich C4 with Ion-Exchanged Zeolites", Ind. Eng. Chem. Res. 2011, 50, 6382-6380.

(Continued)

*Primary Examiner* — Tam M Nguyen
(74) *Attorney, Agent, or Firm* — Mossman, Kumar & Tyler, P.C.

(57) ABSTRACT

Treatment of hydrocarbon streams, and in one non-limiting embodiment refinery distillates, with reducing agents, such as borohydride and salts thereof, alone or together with at least one co-solvent results in reduction of the sulfur compounds such as disulfides, mercaptans, thiophenes, and thioethers that are present to give easily removed sulfides. In one non-limiting embodiment, the treatment converts the original sulfur compounds into hydrogen sulfide or low molecular weight mercaptans that can be extracted from the distillate with caustic solutions, hydrogen sulfide or mercaptan scavengers, solid absorbents such as clay or activated carbon or liquid absorbents such as amine-aldehyde condensates and/or aqueous aldehydes.

13 Claims, No Drawings

(56) References Cited

OTHER PUBLICATIONS

Environmental Catalysts Odorgard, Johnson Matthey Process Technologies, 2011, 1-12.
Harruff, Lewis G., et al., "Improving fractionation lowers butane sulfur level at Saudi gas plant", Oil & Gas Journal, Oct. 21, 1998, vol. 96, Issue 41, 6 pages.
Rohm and Haas: The Sodium Borohydride Digest, www.scribd.com/document/326437122/Sodium-BorohydrideDigest, Oct. 2003, 1-212.
Venmet Borohydride Solution, Product Safety Assessment, The Dow Chemical Company, Aug. 2013, 1-5.
Material Safety Data Sheet, The Dow Chemical Company, Apr. 2013, 1-11.
Shu, Chenhua, et al.,"A novel process for gasoline desulfurization based on extraction with ionic liquids and reduction by sodium borohydride", Fuel, 2014, vol. 121, 72-78.

* cited by examiner

CHEMICAL PROCESS FOR SULFUR REDUCTION OF HYDROCARBONS

CROSS-REFERENCE TO RELATED APPLICATION

This application is a continuation-in-part application from U.S. patent application Ser. No. 15/470,196 filed Mar. 27, 2017, issued Sep. 17, 2019 as U.S. Pat. No. 10,414,989, which in turn claims the benefit of U.S. Provisional Patent Application No. 62/323,120 filed Apr. 15, 2016, both of which are incorporated herein by reference in their entireties.

TECHNICAL FIELD

The present invention relates to the removal of sulfur compounds from hydrocarbon streams, and more particularly relates, in one non-limiting embodiment, to methods for removing sulfur compounds from a hydrocarbon streams using a reducing agent.

TECHNICAL BACKGROUND

Sulfur, generally in the nature of organosulfur molecules, is an undesirable contaminant in many hydrocarbon streams and volumes having hydrocarbon carbon chain lengths of from C1 to C30, some of which may be utilized as or in fuels containing hydrocarbon molecules having C1-C12.

Additives currently used to reduce sulfur content only work on inorganic forms of sulfur (mainly hydrogen sulfide, $H_2S$) or low molecular weight (C1-C4) mercaptans. To remove high molecular weight (C5+) mercaptans, disulfides, thioethers and other sulfur compounds, the literature suggests oxidizing agents, such as a peroxide, e.g. hydrogen peroxide, is needed to convert the sulfur species into water soluble sulfoxides or sulfones which can be extracted from the hydrocarbon.

Future gasoline specifications in the United States require sulfur compounds to be reduced to very low levels. The levels are low enough that gasoline blend components such as butanes containing sulfur compounds will make the finished gasoline fail sulfur limits. Refiners desire to limit their capital expenditures and seek alternatives to the building of additional hydrotreating capacity, so they are seeking alternatives to remove these sulfur compounds from their distillates.

It would be desirable to remove sulfur compounds from refinery distillate streams using an alternative process to those presently in use.

SUMMARY

There is provided in one non-limiting embodiment a method for removing a sulfur compound from a hydrocarbon stream containing the sulfur compound where the method includes contacting the hydrocarbon stream with an amount of an aqueous reducing agent effective to react with the sulfur compound to form at least one reaction product in a treated hydrocarbon stream. The aqueous reducing agent includes from 0 to about 80 vol % of at least one co-solvent based on the total amount of reducing agent and at least one borohydride salt.

In an alternative non-restrictive version there is provided a treated hydrocarbon stream that includes hydrocarbons, at least one sulfur compound, at least one reducing agent, where the at least one reducing agent includes from 0 to about 80 wt % of at least one co-solvent based on the total amount of reducing agent and at least one inorganic borohydride salt, where an amount of a reducing agent is present effective to react with the sulfur compound to form at least one reaction product.

In another non-limiting embodiment the methods are practiced at high pH, where the reducing agent is in an aqueous solution and has a high pH defined as ranging from about 7 to about 14, alternatively at 7 or above. In one non-limiting embodiment, a basic pH aqueous solution contains borohydrides, but these borohydrides are reactive toward acid. Higher pH prevents the borohydride from decomposing by forming hydrogen gas.

DETAILED DESCRIPTION

It has been discovered that treatment of hydrocarbons, particularly refinery distillates, with a reducing agent, in a non-limiting embodiment, a high pH aqueous borohydride, with or without a co-solvent, results in the reduction of the sulfur compounds such as disulfides, mercaptans, thiophenes, and thioethers that are present to give easily removed sulfides. The treatment converts the original sulfur compounds into hydrogen sulfide ($H_2S$) or low molecular weight mercaptans that can be extracted from the distillate with caustic solutions, hydrogen sulfide or mercaptan scavengers or solid absorbents such as clay or activated carbon or liquid absorbents, such as amine-aldehyde condensates and aqueous aldehydes. In one expected non-restrictive practice, the borohydride solution is injected into the distillate in rundown lines from refinery production units to tankage and/or can be injected in recirculation loops of storage tanks. Good mixing of the borohydride with the distillate is helpful to facilitate reaction and additionally there needs to be a downstream separation point to remove the aqueous solution. Separators, centrifuges or even storage tank bottoms are all adequate to collect the aqueous by-products. Optionally passing the treated and dehydrated hydrocarbon through a subsequent filtration or in contact with a solid or liquid absorbent (in non-limiting embodiments, clays, carbon, zeolites, amine-aldehyde condensates and the like) removes any residual borohydride and the reaction product yielding lower sulfur content distillate able to meet all sales specifications. Alternatively, the separation could also be accomplished using an extraction technique such as a contact tower or caustic wash unit.

In another non-limiting version the sulfur compounds can be extracted into the caustic/borohydride or caustic/borohydride/alcohol solution in a single step. Simply shaking the borohydride solutions with the hydrocarbon (e.g. fuel) and allowing the components to separate will reduce the sulfur content of the hydrocarbon. A second or subsequent treatment with a solid absorbent or liquid absorbent can reduce sulfur content even more.

In another non-limiting embodiment with more specificity, a solution of a borohydride in caustic is injected into a hydrocarbon containing organic sulfur compounds such as disulfides (R—S—S—R), thioethers (R—S—R), carbonyl sulfide (COS), thiophenes, or carbon disulfide ($CS_2$). The borohydride is thought to reduce the sulfur compounds to inorganic $H_2S$ or to low molecular weight mercaptans which are then removed from the hydrocarbon by the caustic in the borohydride solution or alternatively by adding an additional $H_2S$ scavenger (including, but not necessarily limited to, triazines; metal carboxylates such as those including the metals Zn, Cu, and/or Fe; oxides, hydroxides or carbonates) to the distillate. The hydrogen sulfide scavengers should be aqueous or alternatively formulated in a hydrocarbon insoluble solvent so the sulfur-containing reaction products can be separated from the hydrocarbon. Any separation equipment used for oil/water separation can be used in the process described herein. A subsequent or final step may be where the treated hydrocarbon is passed through and/or contacted with an absorbent that is used to remove any residual borohydride, sulfur compound or $H_2S$ scavenger to yield a hydrocarbon distillate with a much reduced sulfur content.

It is expected that the borohydrides will be introduced as at least one borohydride salt, which may be an inorganic salt form of borohydride or ammonium salts of borohydride. Other reducing agents besides sodium borohydride include, but are not necessarily limited to, borane ($BH_3$), borane complexes with ethers, amines and other complexing agents, lithium aluminum hydride, sodium hydride, calcium hydride and other metal hydrides may be substituted for the borohydride above. Metal hydrides such as lithium aluminum hydride, sodium hydride and calcium hydride may be too sensitive to air and moisture sensitive in some cases to be used in the application. In other circumstances they may be so strong of a reducing agent that they will reduce the olefins being treated. Catalysts including, but not necessarily limited to, a Lewis acid (e.g. aluminum chloride, ferric chloride, zinc chloride) may also be used to facilitate the reduction of the sulfur compounds.

In another non-limiting embodiment, the borohydride salt may be ammonium salts of borohydride $R^3{}_4N^+BH_4^-$, where $R^3$ are independently C1 to C4 or arylalkyl (benzyl), where the alkyl groups are C1 to C4. In some cases it is desirable to avoid any chance of metals being added to the hydrocarbon. Sodium, calcium and other metals can be harmful to downstream catalysts when treating refinery feedstocks. Using an ammonium cation allows the avoidance of metals.

The sulfides formed by the reduction may be removed via simple gravity separation of an aqueous or other immiscible phase or by use of solid absorbent beds such as metals (zinc, iron, and the like) on absorbents (clay, zeolites, carbon, and the like). Alternatively the sulfides may be removed by contact with liquid absorbents including, but not necessarily limited to, amine-aldehyde condensates and/or aqueous aldehydes, and the like. Treatment can be in stages or a single process. For example if the hydrocarbon contains hydrogen sulfide in addition to the other sulfur compounds, it can be treated first with a hydrogen sulfide scavenger to remove the $H_2S$ and then treated with the borohydride to reduce additional sulfur compounds and then finally filtered or run through an extraction process to remove the reduced sulfur products.

Suitable sulfur compound-containing refinery distillate streams include, but are not necessarily limited to, liquid or gas hydrocarbons selected from the group consisting of C1 to C12 alkanes, including methane, C2 to C12 alkenes, liquefied petroleum gas, natural gas, fuel gas, flare gas, naphtha, gasoline, kerosene and mixtures thereof; possibly up to C16 for diesel fuels. However, the methods described herein are expected to also be effective in oilfield applications, including, but not necessarily limited to, removing sulfur compounds from oilfield condensates, natural gas, and the like, The methods described herein may also be effective in treating natural gas liquids (NGL) or liquid petroleum gas (LPG) within or as it is withdrawn from a storage facility.

The sulfur compounds that may be removed from the refinery distillate streams include, but are not necessarily limited to, mercaptans having the formula R—S—H where R is a linear or branched C1 to C4 alkyl group, carbon disulfide ($CS_2$), carbonyl sulfide (COS), dialkyl sulfides having the formula $R^1$—S—$R^2$ where $R^1$ and $R^2$ are independently linear or branched C1 to C4 alkyl groups, dialkyl disulfides having the formula $R^1$—S—S—$R^2$ where $R^1$ and $R^2$ are as previously defined, and thiophenes, where the thiophenes may be unsubstituted thiophene of the formula:

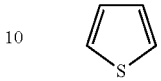

or substituted thiophenes, where the substituents include, but are not necessarily limited to halogens, nitro, C1-C6 haloalkyls, linear or branched C1-C6 alkyl groups, phenyl, C1-C6 carboxylates, and these hydrocarbon groups having heteroatoms including, but not necessarily limited to oxygen, sulfur, and nitrogen.

With more specificity, suitable reducing agents include, but are not necessarily limited to, borane ($BH_3$); diborane ($B_2H_6$); complexes of borane or diborane with Lewis bases selected from the group consisting of ethers, dialkyl sulfides, amines, alcohols, and mixtures thereof; inorganic borohydride salts having the formula $M^1BH_4$ where $M^1$ is selected from the group consisting of Li, Na, and K, or having the formula $M^2(BH_4)_2$ where $M^2$ is selected from the group consisting of Mg, Ca or Zn, ammonium salts as previously described; cyanoborohydrides having the formula $M^1BH_3CN$ where $M^1$ is as previously defined or having the formula $M^2(BH_3CN)_2$ where $M^2$ is as previously defined; organic borohydrides having the formula $M^1BR^3{}_3H$ where M is as previously defined and $R^3$ is independently selected from the group consisting of linear or branched C1 to C3 alkyl groups and a carboxylate group having the formula $R^4C(O)O$— and $R^4$ is selected from the group consisting of linear or branched C1 to C9 alkyl groups; and combinations thereof. That is, there can be combinations of R and $R^4C(O)O$— on the same boron, such that all $R^3$s can be alkyl, all $R^3$s can be $R^4C(O)O$—, or there can be combinations of the two.

Also for the purposes of the present application, the term "caustic" is defined broadly to mean a strong base (alkaline) substance including, but not limited to sodium hydroxide (NaOH), potassium hydroxide (KOH), and lithium hydroxide (LiOH); but also specifically including any compound now known or later discovered to be useful for extracting or otherwise removing a sulfur compound from a refinery distillate fluid stream. However, in another non-limiting embodiment "caustic" is defined as selected from the group consisting of sodium hydroxide, potassium hydroxide, lithium hydroxide, and combinations thereof. It will be appreciated that the fact that a liquid washing phase, which in one non-limiting embodiment is a caustic liquid, does not encompass all liquids that are basic which contain relatively small amounts of an alkali metal hydroxide or alkanolamine, alkyl amine, and/or alkazides to adjust the pH of the liquid. In the caustic liquids used herein, the caustic or basic materials, in the case where alkali metal hydroxide is used in the basic system, the amount of alkali metal hydroxide may be about 50 wt % or less based on the water used to treat the refinery distillate stream; alternatively about 15 wt % or less; and in another non-limiting embodiment, about 12 wt % or less. Many of the suitable caustic solutions will have high levels of KOH and/or NaOH. These caustic solutions have a much higher density than the hydrocarbons being treated to improve separation of the two phases. The density difference between caustic and the hydrocarbon improves the settling rate and gives better separation. The contacting of the reducing agent with the refinery distillate stream may be in an aqueous solution having a pH from about 7 independently to about 14; alternatively a pH from about 10 to about 13.5. In another non-limiting embodiment, the basic aqueous system containing the reducing agent may have a pH of 9 or greater; alternatively 9.5 or greater, and in a different non-limiting embodiment of 10 or greater. In another non-restrictive version, these thresholds may be used together with the pH ranges given previously as alternative thresholds for suitable alternative pH ranges. As noted, these liquids are aqueous. It is fortunate that while borohydrides are strong reducing agents, they may be employed in aqueous solutions.

It will be appreciated that the reducing agents herein exclude metal hydrides such as aluminum hydrides, NaH, LiH, and $CaH_2$, since they are often too water- and/or air-sensitive to be applied in the method described herein.

Water is the typical solvent for the reducing agent, whereas co-solvents include, but are not necessarily limited to, Lewis bases selected from the group consisting of ethers, dialkyl sulfides, amines, alcohols, and mixtures thereof. More specifically, when the co-solvent is an alcohol, suitable alcohols include, but are not necessarily limited to, C1-C8 mono and poly hydric alcohols including, but not particularly restricted to, methanol (MeOH), ethanol, 2-propanol, butanol, 2-ethylhexanol, ethylene glycol, diethylene glycol, and glycerol. In one suitable non-limiting embodiment the co-solvent is methanol. Although the method is sometimes described herein with methanol as the only co-solvent, it will be appreciated that other co-solvents may be used in place of or together with methanol.

Co-solvents such as methanol help transfer the sulfur compounds to the caustic solution. In one non-limiting theory, many of the sulfur compounds formed are not soluble in the caustic used with the borohydride. Adding methanol increases the solubility of these sulfur materials and allows for better extraction from the hydrocarbon and into the reducing agent additive. Methanol is soluble in the caustic/borohydride solution but it stays with the reducing agent additive when the reducing agent is contacted with a fuel. It was found that the volume of the caustic/borohydride/alcohol solution remains the same after contact with the hydrocarbon (50 mls in Tables VI, VII, and VIII below). It was originally thought that some of the alcohol would be lost to the hydrocarbon phase but the tests showed complete separation of the two phases and the original volumes of hydrocarbon and scavenger returned.

In a non-limiting embodiment, the amount of co-solvent in the reducing agent a minimum of 0 vol % co-solvent (e.g. alcohol) (inorganic borohydride salt alone) independently to a maximum of 80 vol % co-solvent (e.g. alcohol) in the blend; in another non-restrictive version from about 10 vol % independently to about 70 vol %, alternatively from about 20 vol % independently to about 60 vol % methanol in the blend.

In some embodiments of the methods herein, a refinery distillate stream is treated with a reducing agent. In a non-restrictive example, carbonyl sulfide (COS) can be removed from a refinery distillate stream, by the addition of sodium borohydride ($NaBH_4$) as the additive. When COS gas is present in a solution of $NaBH_4$, the COS will react with the $NaBH_4$ and the reaction is irreversible. The reaction can be illustrated as follows:

$$O{=}C{=}S + H^- \rightarrow O{=}CH{-}S^- \text{ or } {^-}O{-}CH{=}S \quad (1)$$

The reaction products are a more polar species, that is, a more water-soluble species and can be washed away by the aqueous caustic.

The effective amount of reducing agent added is any amount that is effective to bind up and/or react with the sulfur compound and at least partially convert it to a reaction product that can be removed. In one non-restrictive version, the effective amount of the reducing agent is up to two times the stoichiometric ratio of the reducing agent to the sulfur compound; alternatively, the effective amount ranges from about 0.8 to about 1.8 times the stoichiometric ratio of the reducing agent to the sulfur compound. In another non-limiting embodiment, the effective amount of $NaBH_4$, or other reducing agent, is a molar ratio of $NaBH_4$ to COS of from about 0.02:1 independently to about 50:1 based on the amount of sulfur compound in the process stream; alternatively, the molar ratio ranges from about 0.1:1 independently to about 40:1. The word "independently" as used with respect to a range herein means that any lower threshold may be used with any upper threshold to provide a suitable alternative range. The theoretical amount is a 1:1 mole ratio of $NaBH_4$ to COS, as shown in reaction (1). In one non-limiting embodiment the amount of $NaBH_4$ to COS is in excess of a mole ratio of 1:1.

In some cases, the reducing agent solution will be contacted with the hydrocarbon and it will be both scavenger which converts the sulfur compounds present into another form and it will also be the solution which extracts the sulfur compounds formed (reaction products) away from the hydrocarbon, that is, in a single step. In other, different cases, a second treatment of the hydrocarbon with a solid or liquid absorbent will be conducted to remove the sulfur compounds formed by the borohydride (reaction products). That is, in some non-limiting embodiments the hydrocarbon will simply be contacted with the reducing agent (e.g. borohydride) solution and it will be both scavenger and absorbent. In other different, non-restrictive embodiments, the treated hydrocarbon will be passed through the solid/liquid absorbent to be sure all sulfur compounds (and scavenger) are removed. With respect to dose rates, if the reducing agent (e.g. borohydride) solution is simply injected into a hydrocarbon stream a ppm of scavenger to ppm of sulfur ratio based on the chemistry may be provided. However if the hydrocarbon is bubbled through a solution of the reducing agent (e.g. borohydride) then the amount of reducing agent solution will be relatively large in the tower as compared with the relatively small amount of hydrocarbon migrating through the aqueous solution of reducing agent In the non-limiting case of the reducing agent (in this case borohydride) solution being directly injected into the sour hydrocarbon, one non-restrictive ppm dosage range would be from about 0.5 independently to about 10 ppm borohydride per ppm of sulfur to be removed; alternatively from about 1 independently to about 5 ppm borohydride per ppm sulfur to be removed.

In tower applications where sour hydrocarbon is bubbled through the borohydride solution, the ratio will be higher as there are only small bubbles of the hydrocarbon migrating up through the borohydride solution in the tower. There will be a relatively large volume of the borohydride solution present since it fills the contact tower and only a relatively small amount of sulfur compound present in the small bubbles of the hydrocarbon migrating their way through the borohydride solution. In this latter case, the ratio of borohydride solution to hydrocarbon can range from about 95 vol % borohydride scavenger independently to as low as 1 vol % borohydride to sour gasoline; alternatively on the order of about 10 independently to about 50 vol % borohydride solution to sour hydrocarbon. It will be appreciated that for a different reducing agent than borohydride, these dosage ranges will be different due to different stoichiometery.

Generally, the additives will be present at a level in the treated refinery distillate stream such that the concentration of sulfur compound in the stream is lowered to from about 1 or less than 1 independently to about 5 ppm. In other embodiments the concentration after treatment is from about 0.1 independently to about 100 ppm. In one non-limiting embodiment, there may remain from about 1 to about 2 ppm sulfur in the treated hydrocarbon and gasoline specifications may still be met. In one non-limiting embodiment the highest levels of sulfur expected to be treated in the hydrocarbon stream will be on the order of 500 ppm and it may be desired to reduce sulfur content to less than 1 ppm. Alternatively an expected starting sulfur content of 100 ppm or less which can be reduced to 3 ppm or less, and in a different non-restrictive version the starting sulfur content may be about 50 or less, which can be reduced to 5 ppm or less.

The temperature range for the contacting by the reducing agent will only be limited by the additive properties. The stream being treated cannot be so hot that the water in the additive is flashed off and leave solid borohydride behind. Conversely, the stream cannot be so cold that the additive freezes and does not mix with the hydrocarbon stream. In general, it is expected that relatively hotter will be better than relatively colder since kinetics improve as temperature increases, but again in general, the temperature cannot be so hot that the solvent (water) flashes off.

In addition to the additives already described, the additives used herein may include other compounds known to be useful in sulfur compound removal methods such as dispersants, defoamers, and the like. Any compound that does not have an undesirable interaction with the additive's ability to reduce or remove the sulfur compound may be used with at least some embodiment of the methods and compositions described herein. A defoamer in particular might be used if a gas is being treated. Additionally, a demulsifier may be employed if the separation step used involves settling in a storage tank. For instance, there could be some emulsion present that was generated by contact of the aqueous and hydrocarbon phases. A demulsifier will help break the water away from the hydrocarbon.

To reduce the sulfur content of the treated refinery distillate stream, a separation step is required in some non-limiting embodiments. The separation can utilize solid absorbents like carbon, clay and zeolites or alternatively the separation can utilize an extraction with caustic solutions or water. The extraction solvent can optionally be part of the borohydride additive (i.e. the borohydride may be formulated in caustic like the Baker Hughes Additive C additive used in the lab test) or it may be present in a contact tower, settling tank, water/caustic wash vessel, and the like. Small particle size absorbents (powdered carbon vs. carbon pellets) are advantageous in an absorbent. Suitable powders may have a particle size of equal to or less than 0.075 mm, suitable granular sizes may have a particle size of 1.2-1.4 mm and suitable pellets may have a minimum size of 4 mm. The only necessary condition for an extraction solvent is that it should have a pH of neutral or basic (i.e. equal to or greater than 7.0). Acids decompose borohydrides, so an acidic pH would cause some problems of hydrogen generation in the process. Suitable clays include, but are not necessarily limited to, attapulgite, montmorillonite, bentonite, and the like.

As noted, removing the reaction products from the treated refinery distillate stream may include any method known to those skilled in the relevant art, such as by using a clay and/or carbon. The use of carbon, such as activated carbon, carbon powder, granulated carbon, other particulate carbon, is a consideration for the separation step because it has been discovered that more sulfur can be removed by carbon when the hydrocarbon has been treated with the reducing agent described herein. Without being limited to any specific explanation, this may be because the reducing agent modifies the sulfur compounds present such that they are better removed by absorption on the carbon media. In the present method, the sulfur compounds are modified before contact with the carbon and the result is that even the modified carbon can absorb more of the sulfur species produced with the reducing agents described herein. The amount of absorbent needed will vary depending on the type of sulfur compounds being removed. Some sulfur compounds with large "R" groups, i.e. alkyl groups, for example will take up more space on the carbon than sulfur compounds with small "R" groups. The overall capacity of the absorbent will depend on the amount of each sulfur compound present in the hydrocarbon refinery distillate stream being treated.

With respect to the optional liquid absorbents to remove the reaction products formed by the treatment with the caustic/borohydride solution, suitable amine-aldehyde condensates include, but are not necessarily limited to monoethanolamine (MEA) triazines, methylamine (MA) triazines. Suitable aqueous aldehyde solutions include, but are not necessarily limited to, glyoxal, glycolaldehyde, glutaraldehyde and the like. The amount of liquid absorbent may range from about 1 independently to about 90% by volume of hydrocarbon being treated; alternatively from about 10 independently to about 50% by volume of the hydrocarbon being treated. The Examples 52-60 reported below used 10% volume of liquid absorbent to 90% hydrocarbon which fits in the narrower range. Contacting the hydrocarbon with just the caustic solution works well, but the capacity to extract the reaction products formed in the hydrocarbon is limited. This leads to a high replacement rate of the additive if only the caustic solution alone is used. The reaction products such as mercaptide ions may stay in the treated hydrocarbon as the caustic/hydrocarbon solution separates. It should be noted that not all liquid absorbents work. Inorganic oxidizers such as ferric chloride and simple neutralizing amine, such as methyldiethanolamine, have been tried and they do not work. It should be noted that when the methanol co-solvent is used, it has to be part of the borohydride solution. It cannot be used in a separate step like the materials discussed immediately above as it is soluble in the fuel and does not form a separate phase that can be removed in the extraction.

The process described herein also has the potential to remove higher mercaptans which current scavengers do not remove. Thus, higher boiling fractions can be treated to remove these corrosive materials using this method.

The following examples are provided to illustrate the present method. The examples are not intended to limit the scope of the present method and they should not be so interpreted. Amounts are in weight parts or weight percentages unless otherwise indicated.

Sulfur Scavenger Test Procedure

1.) Light Virgin Naphtha (LVN) as freshly received from refinery is dosed with additional sulfur (S) compounds. These include 1-butanethiol, dimethyl disulfide, diethyl sulfide, and carbon disulfide.
   a. The desired S compound is injected directly into a measured volume of LVN sample using an appropriately sized syringe at dose required to attain targeted ppm level (i.e., 100-1,000+ ppm)
   b. The syringe (i.e., 10 uL-1 mL) shall reach below the surface of the LVN sample as to limit escape into the container headspace during transfer.
   c. Use a different clean syringe/microdispenser/cannula for each S compound to avoid the potential for cross-contamination.
   d. The container (e.g., 1 L clear glass bottle with screw-on cap) shall be filled close to the top to limit the more volatile S compounds from evolving to the vapor phase.
   e. To ensure a homogenous mix, place the capped bottle in a horizontal position on an orbital shaker at 220 rpm for 30 seconds.
2.) Using an appropriately sized syringe, dose empty (e.g. 6 oz. graduated prescription bottle) with desired chemical additive.
   a. In this case, either Baker Hughes Additive C (12.5% by wt. sodium borohydride) or Baker Hughes Additive A (45% by wt. potassium hydroxide)
   b. Fill dosed bottle to mark (e.g. 100 mL) with LVN to achieve targeted treat rate (i.e., ppm v/v)
3.) Mix well to insure contact of chemical additive with S compounds in the LVN.
   a. Lay capped bottles in a horizontal position on an orbital shaker set at 220 rpm for 2 hour.
   b. At this point, if the sample is to be filtered then go immediately to Step #4, otherwise proceed to Step #3c and then onto Step #5.
   c. After thoroughly mixing let samples sit quietly over-night (about 16 hours) to allow any aqueous reaction products to potentially settle out.
4.) Filtered samples are gravimetrically allowed to migrate through activated carbon.
   a. w/w ratio 1:3.2 carbon: LVN.
   b. Set a small amount of clean glass wool (0.7-0.8 gm) in the bottom of a funnel (e.g. a 100 mm powder funnel) to hold the powdered carbon in place.
   c. Weigh 25 gm carbon into funnel.
   d. Slowly and evenly pour LVN through carbon filter.
   e. Collect filtered LVN into smaller bottle (e.g. a 2 oz. clear glass bottle with a screw-on cap) until filled to top to limit headspace.
5.) Labeled sample bottle is then tested for weight percent (or ppm) total sulfur and/or sulfur speciation.
   a. Do not agitate/re-mix sample bottle.
   b. Aliquot for testing will be drawn from upper portion of sample and any aqueous bottoms should not be disturbed.
   c. Total Sulfur (i.e., Sulfur in Oil) to be determined by Energy Dispersive X-Ray Fluorescence (ED-XRF) (i.e., use the ASTM D4294 method).
   d. Sulfur Speciation to be determined by Gas Chromatography—Sulfur Selective Detection (GC-SSD) (i.e., use the ASTM D5623 method).

Examples 1-23

The Sulfur Scavenger Test Procedure described above was used to measure the impact of a sodium borohydride additive designated Additive C, which was 12 wt % sodium borohydride in 40 wt % NaOH in water. The results are given in Table I. Abbreviations are given below Table I.

TABLE I

EXAMPLES 1-20
Effect of Additive C Additive on Sulfur Removal

| Ex. | Additive | Dose (ppm) | Weight % S | Comment | % S Removed |
|---|---|---|---|---|---|
| 1 | Naphtha blank (untreated) | 0 | 0.383 wt % | Baseline | 0% |
| 2 | Additive A | 300 | 0.348 wt % | Small level of activity with caustic alone | 9% |
| Test Conditions: Naphtha containing 1000 ppm C4SH + 1000 ppm DMDS + 1000 ppm DES + 1000 ppm CS2. Test temp = Room Temperature (RT, ~75° F.) | | | | | |
| 3 | Naphtha blank (untreated) | — | 0.512 wt % | Baseline | 0% |
| 4 | Additive A | 3,000 | 0.346 wt % | Higher dose of caustic gives better activity | 32% |
| Test Conditions: Naphtha containing 1000 ppm C4SH + 1000 ppm DMDS + 1000 ppm DES + 1000 ppmCS2. Test temp = RT (~75° F.) | | | | | |
| 5 | Additive C | 4,000 | 0.356 wt % | Baseline | 0% |
| 6 | Additive C | 6,000 | 0.260 wt % | Higher dose of Additive C = better performance | 27% |
| 7 | Additive C | 12,000 | 0.258 wt % | Higher dose of Additive C = leveling off performance | 28% |
| Test Conditions: Naphtha containing 3000 ppm DMDS. Test temp = RT (~75° F.) | | | | | |
| 8 | Naphtha blank (untreated) | — | 87.3 ppm | Baseline | 0% |
| 9 | Additive C | 100 | 85.8 ppm | Small level of activity on removal of DES | 2% |
| 10 | Additive C | 500 | 88.1 ppm | No activity on DES removal | −1% |
| 11 | Additive C | 1,000 | 84.1 ppm | Higher dose of Additive C = better performance | 4% |

TABLE I-continued

EXAMPLES 1-20
Effect of Additive C Additive on Sulfur Removal

| Ex. | Additive | Dose (ppm) | Weight % S | Comment | % S Removed |
|---|---|---|---|---|---|
| \multicolumn{6}{l}{100 ppm DES only added to each sample as only sulfur compound. Test temp = RT (~75° F.)} |
| 12 | Naphtha blank (untreated) | — | 290.1 ppm | Baseline | 0% |
| 13 | Additive C | 100 | 300 ppm | No activity on CS2 removal | −3% |
| 14 | Additive A | 100 | 300.3 ppm | No activity on CS2 removal | −4% |
| \multicolumn{6}{l}{100 ppm CS2 only added to each sample as only sulfur compound. Test temp = RT (~75° F.)} |
| 15 | Naphtha blank (untreated) | — | 92.4 ppm | Baseline | 0% |
| 16 | Additive C | 100 | 89.6 ppm | Small level of activity on C4SH removal | 3% |
| 17 | Additive A | 100 | 88 ppm | Small level of activity on C4SH removal | 5% |
| \multicolumn{6}{l}{100 ppm C4SH only added to each sample as only sulfur compound. Test temp = RT (~75° F.)} |
| 18 | Naphtha blank (untreated) | — | 190.5 ppm | Baseline | 0% |
| 19 | Additive C | 100 | 94.5 ppm | Excellent removal of CS2 | 50% |
| 20 | Additive A | 100 | 192.4 ppm | No activity | −1% |
| \multicolumn{6}{l}{100 ppm DMDS only added to each sample as only sulfur compound. Test temp = RT (~75° F.)} |

Additive A = 45% KOH in water
Additive B = zinc octanoate
Additive C = 12% sodium borohydride in 40% NaOH in water
Additive D = 50% aluminum chloride hydroxide in water
Additive E = 31% polyaluminum chloride in water
CS2 = Carbon disulfide
C4SH—n-butyl mercaptan
DES = Diethylsulfide
DMDS = Dimethyldisulfide

TABLE 11

EXAMPLES 21-33
Carbon Filtration Used to Remove S Species Present/Formed by Additive C

| Ex. | Additive | Dose (ppm) | Weight % S | Comment | % S Removed |
|---|---|---|---|---|---|
| 21 | Carbon filtered, untreated naphtha | — | 0.129 wt % | Baseline | 0% |
| 22 | Additive C | 3,000 | 0.109 wt % | Additive C helps carbon remove S Species | 16% |
| 23 | Additive A | 3,000 | 0.202 wt % | Caustic alone hurts S removal by carbon | −57% |
| \multicolumn{6}{l}{Test Conditions: Naphtha containing 1000 ppm C4SH + 1000 ppm DMDS + 1000 ppm DES + 1000 ppm CS2 1:4 ratio filter media to naphtha. Test temp = RT (~75° F.)} |
| 24 | Carbon filtered, untreated naphtha | — | 140 ppm | Baseline | 0% |
| 25 | Additive C | 100 | 112.5 ppm | Good activity on CS2, Additive C helps carbon remove S species | 20% |
| 26 | Additive A | 100 | 135.4 ppm | No/poor activity | 3% |
| \multicolumn{6}{l}{100 ppm CS2 only added to each sample as only sulfur compound, 1:4 ratio filter media to naphtha for filtration procedure. Test temp = RT (~75° F.)} |
| \multicolumn{6}{l}{100 ppm DES only added to each sample as only sulfur compound, 1:4 ratio filter media to naphtha for filtration procedure. Test temp = RT (~75° F.)} |
| 27 | Carbon filtered, untreated naphtha | — | 106.1 ppm | Baseline | 0% |
| 28 | Additive C | 100 | 34.5 ppm | Good activity on DMDS, Helps carbon removal of DMDS | 67% |

TABLE II-continued

EXAMPLES 21-33
Carbon Filtration Used to Remove S Species Present/Formed by Additive C

| Ex. | Additive | Dose (ppm) | Weight % S | Comment | % S Removed |
|---|---|---|---|---|---|
| 29 | Additive A | 100 | 37.9 ppm | Caustic slightly less active in helping carbon remove DMDS species | 64% |

100 ppm DMDS only added to each sample as only sulfur compound, 1:4 ratio filter media to naphtha for filtration procedure. Test temp = RT (~75° F.)

| Ex. | Additive | Dose (ppm) | Weight % S | Comment | % S Removed |
|---|---|---|---|---|---|
| 30 | Additive C + Carbon filtered | 4,000 | 0.268 wt % | Baseline | 0% |
| 31 | Additive C + Additive B + Carbon filtered | 4,000 + 2,000 | 0.172 wt % | Zinc Octanoate helps improve DMDS removal by Additive C + carbon filtering | 36% |
| 32 | Additive C + Additive D + Carbon filtered | 4,000 + 2,000 | 0.152 wt % | Aluminum salts help improve DMDS removal by Additive C and Carbon filtering | 43% |
| 33 | Additive C + Additive E + Carbon filtered | 4,000 + 2,000 | 0.186 wt % | Aluminum salts help improve DMDS removal by Additive C and Carbon filtering | 31% |

3000 ppm Dimethyl disulfide (DMDS) only sulfur compounds added to give wt % sulfur listed, 1:4 ratio filter media to naphtha. Test temp = RT (~75° F.)

TABLE III

EXAMPLES 34-42
Comparison of Common Filter Media to Remove S Species

| Ex. | Additive | PPM Sulfur | Comment | % S Removed |
|---|---|---|---|---|
| 34 | Blank @ 75° F. | 613.5 ppm | Baseline | 0% |
| 35 | Blank @ 75° F. filtered through carbon powder | 291 ppm | Powdered Carbon is best filter media for S removal | 53% |
| 36 | Blank @ 75° F. filtered thru granular carbon | 595.2 ppm | Poor S removal by granular carbon filter media | 3% |
| 37 | Blank @ 75° F. filtered thru carbon powder | 347.2 ppm | Powdered Carbon is best filter media for S removal | 43% |
| 38 | Blank @ 75° F. + filtered thru granular carbon | 540 ppm | Poor S removal by granular carbon filter media | 12% |
| 39 | Blank @ 75° F. filtered thru granular carbon | 567.9 ppm | Poor S removal by granular carbon filter media | 7% |
| 40 | Blank @ 75° F. + filtered thru carbon pellets | 592 ppm | Poor S removal by carbon pellet filter media | 4% |
| 41 | Blank @ 75° F. + filtered thru fine clay attapulgite | 586.9 ppm | Poor S removal by clay filter media | 4% |
| 42 | Blank @ 75° F. + filtered thru coarse clay attapulgite | 639 ppm | Poor S removal by clay filter media | −4% |

Examples 43-51

Liquid Absorbents of Reaction Products

In these experiments, 10 mls of a commercial aqueous sodium borohydride solution was added to a separatory funnel with 90 mls of sour gasoline. The mixture was shaken by hand 100 times and then allowed to separate. The top hydrocarbon phase was sampled and tested by ASTM D 4952-02 (also known as the doctor test) for active sulfur compounds and also analyzed for total mercaptan content by ASTM D3227. The doctor test is a common method used in the industry to rate the corrosivity of a hydrocarbon toward metals like copper and is a common specification for hydrocarbons. Customers will run the test and if the hydrocarbon fails the test, they will know that it contains active or corrosive sulfur compounds that have to be treated before the hydrocarbon can be put in a pipeline, for example. After washing the gasoline with the borohydride solution, the same gasoline was washed (shaken 100 times by hand) a second time with 10 mls of a 48% active solution of MEA triazine in water. The hydrocarbon phase was allowed to separate and then was sampled and analyzed by the doctor test and ASTM D3227. The results are shown in Table IV.

TABLE IV

Examples 43-47—Na Borohydride + MEA Triazine

| Ex. | Borohydride solution (mls) | MEA triazine absorbent (mls) | Volume of gasoline (mls) | Doctor test result | Mercaptan content (ppm) | Comment |
|---|---|---|---|---|---|---|
| 43 | — | — | — | Fail | 80.4 | Untreated sour gasoline failed the doctor test and had a mercaptan content of 80.4 ppm |
| 44 | — | — | 90 | Fail | 78.7 | Gasoline washed with only 10 mls of water without scavenger or absorbent—water is not effective in reducing mercaptan content or activity of hydrocarbon on the doctor test. |
| 45 | 0 | 10 | 90 | Fail | 59.4 | The liquid adsorbent (MEA triazine) removes some mercaptan from the gasoline but not enough to give a doctor test pass |
| 46 | 10 | 0 | 90 | Fail | 23.2 | The borohydride solution alone significantly reduces gasoline mercaptan content but still not by enough to give a passing rating on the doctor test |
| 47 | 10 | 10 | 90 | Pass | 16.5 | Washing the gasoline with the borohydride solution and then washing the same hydrocarbon a second time with MEA triazine solution reduced the mercaptan content enough that passing doctor test was obtained. |

In a second set of experiments, both the borohydride and the MEA triazine solutions from the Examples 43-47 above were reused and shaken with fresh sour gasoline to see how many cycles could be run and still get a passing doctor test. Thus, the same borohydride solution separated from the tests above was shaken with fresh sour gasoline, allowed to separate, sampled and tested by doctor test and ASTM D3227. If the gasoline failed the doctor test, it was shaken a second time with only the MEA triazine solution, allowed to separate, sampled and tested by doctor test and for mercaptan content. The cycles of using spent borohydride and MEA triazine were repeated until a failing doctor test was no longer obtained. Results are presented in Table V.

TABLE V

Examples 48-51—Na Borohydride + MEA Triazine Continued

| Ex. | Borohydride solution (mls) | MEA triazine solution (mls) | Volume of gasoline (mls) | Doctor test result | Mercaptan content (ppm) | Comment |
|---|---|---|---|---|---|---|
| 48 | 10 | 0 | 90 | Fail | 24.7 | Borohydride solution from Ex. 55 above shaken with fresh sour gasoline |
| 49 | (10) | 10 | 90 | Pass | 17.3 | Gasoline from Ex. 57 shaken with MEA triazine solution from Ex. 54 above |
| 50 | 10 | 0 | 90 | Fail | 25.9 | Borohydride solution from Ex. 57 shaken with fresh sour gasoline |
| 51 | (10) | 10 | 90 | Fail | 21.6 | Gasoline from Ex. 59 shaken with MEA triazine from Ex. 58 above |

The tests in Table V show that while the borohydride solution does reduce the active sulfur content of the gasoline, it leaves enough sulfur compounds behind that the treated gasoline fails the doctor test. Washing with a liquid adsorbent like the MEA triazine solution removes sulfur compounds left behind by the borohydride washing and allows the gasoline to pass the test. The spent scavenger and absorbent can be reused for a number of cycles which noticeably improves the economics of any treatment.

As discussed previously, it has been discovered that adding an alcohol or other Lewis base, such as methanol to the borohydride/caustic formulation improves sulfur reduction dramatically. The sulfur content of the fuels reported in Table VI for Examples 52-56 are all much lower after treatment with the Formulation A/methanol blend than with simply the Formulation A itself.

Formulation A is composed of:
12.5% sodium borohydride
40% sodium hydroxide
47.5% water The Formulation/methanol blend is a solution of:
5% sodium borohydride
16% sodium hydroxide
60% methanol
19% water

TABLE VI

Examples 52-56 - Na Borohydride With and Without Methanol

| Ex. | Customer | Fuel Type | Untreated sulfur content (ppm) | Treated with Formulation A sulfur content (ppm) | Treated with Formulation A/methanol blend sulfur content (ppm) |
|---|---|---|---|---|---|
| 52 | 1 | Gasoline | 38 | 33 | 9 |
| 53 | 2 | Gasoline | 726 | 604 | 280 |
| 54 | 3 | Gasoline | 644 | 454 | 213 |
| 55 | 4 | Diesel | 514 | 514 (no sulfur reduction) | 475 |
| 56 | 5 | Kerosene | 439 | 439 (no sulfur reduction) | 350 |

Additional data on methanol bends are provided in Tables VII and VIII below.

TABLE VII

Examples 57-61 - Na Borohydride With and Without Methanol

| Ex. | Sample | Co-solvent (mls) | Total Sulfur Content (ppm) |
|---|---|---|---|
| 57 | Untreated Gasoline | none | 38.86 |
| 58 | Form. A (50 mls) | None | 32.17 |
| 59 | Form. A (10 mls) | Methanol (40 mls) | 9.34 |
| 60 | Form. A (20 mls) | Methanol (30 mls) | 8.69 |
| 61 | Form. A (25 mls) | Methanol (25 mls) | 11.99 |

TABLE VIII

Examples 62-76 - Na Borohydride With and Without Methanol

| Ex. | Sample | Co-solvent (mls) | Total Sulfur Content (ppm) |
|---|---|---|---|
| 62 | Untreated Gasoline # 1 | None | 38 |
| 63 | Form. A (50 mls) | None | 33 |
| 64 | Form. A (20 mls) | Methanol (30 mls) | 9 |
| 65 | Untreated Gasoline # 2 | None | 726 |
| 66 | Form. A (50 mls) | None | 604 |
| 67 | Form. A (20 mls) | Methanol (30 mls) | 280 |
| 68 | Untreated Gasoline # 3 | None | 644 |
| 69 | Form. A (50 mls) | None | 454 |
| 70 | Form. A (20 mls) | Methanol (30 mls) | 213 |
| 71 | Untreated Diesel | None | 514 |
| 72 | Form. A (50 mls) | None | 514 (no sulfur reduction) |
| 73 | Form. A (20 mls) | Methanol (30 mls) | 475 |
| 74 | Kerosene | None | 439 |
| 75 | Form. A (50 mls) | None | 439 (no sulfur reduction) |
| 76 | Form. A (20 mls) | Methanol (30 mls) | 350 |

As noted, water is the solvent in the aqueous reducing agents. When the reducing agent is combined in a 40/60 ratio with a co-solvent such as methanol a new formulation is made, in a non-limiting embodiment containing 5 vol % sodium borohydride, 16 vol % sodium hydroxide, 19 vol % water and 60 vol % methanol. The methanol becomes a co-solvent that has been found to help remove sulfur compounds from the hydrocarbon where with the reducing agent formulation by itself (without the co-solvent), water in the caustic is the only solvent used to extract the sulfur compounds formed by the caustic/borohydride. It has been found that by adding the methanol to the formulation it works better than just using methanol as a separate extraction material, like the amine-aldehyde condensates or aldehydes mentioned above since methanol is soluble in most hydrocarbons treated by the methods described herein. When methanol is mixed with a fuel, it dissolves into the hydrocarbon and a second phase is not formed. When the reducing agent/methanol mixture is mixed with the hydrocarbon, a separate phase does form which allows separation of the sulfur compounds extracted into the phase from the hydrocarbon.

In the foregoing specification, the invention has been described with reference to specific embodiments thereof, and has been demonstrated as effective in providing configurations, methods, and compositions for removing sulfur compounds from refinery distillate streams containing them, for instance as demonstrated in the results of the Tables. However, it will be evident that various modifications and changes can be made thereto without departing from the broader scope of the invention as set forth in the appended claims. Accordingly, the specification is to be regarded in an illustrative rather than a restrictive sense. For example, the type of refinery distillate streams, the amounts and ratios of reducing agents, reaction products, sulfur compounds, treatment procedures, solvents, co-solvents, reaction parameters, solid absorbents, liquid absorbents, and other components and/or conditions falling within the claimed parameters, but not specifically identified or tried in a particular method, are expected to be within the scope of this invention. Further, it is expected that the method may change somewhat from one application to another and still accomplish the stated purposes and goals of the methods described herein.

The present invention may suitably comprise, consist or consist essentially of the elements disclosed and may be practiced in the absence of an element not disclosed. For instance, there may be provided a method for removing a sulfur compound from a hydrocarbon stream containing the sulfur compound, where the method comprises, consists essentially, of or consists of contacting the hydrocarbon stream with an amount of an aqueous reducing agent effective to react with the sulfur compound to form at least one reaction product in a treated hydrocarbon stream, where the reducing agent comprises, consists essentially of, or consists of from 0 to about 80 vol % of at least one co-solvent based on the total amount of reducing agent, and at least one borohydride salt.

In another non-limiting instance, there may be provided a treated hydrocarbon stream comprising, consisting essentially of, or consisting of, hydrocarbons, at least one sulfur compound, at least one reducing agent comprising, consisting essentially of, or consisting of from 0 to about 80 wt % of at least one co-solvent based on the total amount of reducing agent and at least one inorganic borohydride salt, where an amount of a reducing agent is present effective to react with the sulfur compound to form at least one reaction product As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

As used herein, relational terms, such as "first," "second," "top," "bottom," "upper," "lower," "over," "under," etc., are used for clarity and convenience in understanding the disclosure and do not connote or depend on any specific preference, orientation, or order, except where the context clearly indicates otherwise.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" in reference to a given parameter is inclusive of the stated value and has the meaning dictated by the context (e.g., it includes the degree of error associated with measurement of the given parameter).

What is claimed is:

1. A method for removing a sulfur compound from a hydrocarbon stream containing the sulfur compound, the method comprising:
    contacting the hydrocarbon stream with an amount of a liquid, aqueous reducing agent effective to react with the sulfur compound to form at least one reaction product in a treated hydrocarbon stream;
    where the aqueous reducing agent comprises:
        from about 10 to about 80 vol % of at least one co-solvent based on the total amount of reducing agent, where the at least one co-solvent is a Lewis base co-solvent selected from the group consisting of ethers, dialkyl sulfides, amines, mono- and polyhydric alcohols, and mixtures thereof; and
        at least one borohydride salt.

2. The method of claim 1 where the sulfur compound is selected from the group consisting of mercaptans having the formula R—S—H where R is a linear or branched C1 to C4 alkyl group, carbon disulfide ($CS_2$), carbonyl sulfide (COS), dialkyl sulfides having the formula $R^1$—S—$R^2$ where $R^1$ and $R^2$ are independently linear or branched C1 to C4 alkyl groups, dialkyl disulfides having the formula $R^1$—S—S—$R^2$, unsubstituted and substituted thiophenes, and combinations thereof.

3. The method of claim 1 where the hydrocarbon stream comprises liquid or gas hydrocarbons selected from the group consisting of C1 to C12 alkanes, C2 to C12 alkenes, liquefied petroleum gas, natural gas, fuel gas, flare gas, naphtha, gasoline, kerosene, diesel fuel, and mixtures thereof.

4. The method of claim 1 where the co-solvent is selected from the group consisting of a mono- and polyhydric alcohols having from 1 to 8 carbon atoms.

5. The method of claim 1 where the borohydride salt is selected from the group consisting of:
    inorganic borohydride salts having the formula $M^1BH_4$ where $M^1$ is selected from the group consisting of Li, Na, and K or having the formula $M^2(BH_4)_2$ where $M^2$ is selected from the group consisting of Mg, Ca, and Zn;
    ammonium salts of borohydride having the formula $R^3_4N^+BH_4^-$, where $R^3$ are independently C1 to C4 or arylalkyl (benzyl), where the alkyl groups are C1 to C4; and
    combinations thereof.

6. The method of claim 1 where in contacting the hydrocarbon stream with the reducing agent, the reducing agent is aqueous and has a pH ranging from about 7 to about 14.

7. The method of claim 2 where contacting the hydrocarbon stream with the reducing agent is conducted in the presence of a base selected from the group consisting of sodium hydroxide, potassium hydroxide, and combinations thereof.

8. The method of claim 1 where the effective amount of the reducing agent is up to two times the stoichiometric ratio of the reducing agent to the sulfur compound.

9. The method of claim 1 further comprising removing the at least one reaction product from the treated hydrocarbon stream, where removing the at least one reaction product from the hydrocarbon stream comprises a procedure selected from the group consisting of:
    passing the treated hydrocarbon stream through a bed containing a solid absorbent selected from the group consisting of clay, carbon, a zeolite, and combinations thereof; and
    washing the treated hydrocarbon stream with a liquid absorbent selected from the group consisting of amine-aldehyde condensates, aqueous aldehydes and combinations thereof.

10. The method of claim 1 where the co-solvent is present from about 20 to about 60 vol % of at least one co-solvent based on the total amount of reducing agent.

11. A method for removing a sulfur compound from a hydrocarbon stream containing the sulfur compound, the method comprising:

contacting the hydrocarbon stream with an amount of a reducing agent effective to react with the sulfur compound to form at least one reaction product in a treated hydrocarbon stream; and removing the at least one reaction product from the treated hydrocarbon stream; where:

the reducing agent comprises:

from about 10 to about 80 vol % of at least one co-solvent based on the total amount of reducing agent; and at least one inorganic borohydride salt;

the hydrocarbon stream comprises liquid or gas hydrocarbons selected from the group consisting of C1 to C12 alkanes, C2 to C12 alkenes, liquefied petroleum gas, natural gas, fuel gas, flare gas, naphtha, gasoline, kerosene, diesel fuel, and mixtures thereof; and the sulfur compound is selected from the group consisting of mercaptans having the formula R—S—H where R is a linear or branched C1 to C4 alkyl group, carbon disulfide ($CS_2$), carbonyl sulfide (COS), dialkyl sulfides having the formula $R^1$—S—$R^2$ where $R^1$ and $R^2$ are independently linear or branched C1 to C4 alkyl groups, dialkyl disulfides having the formula $R^1$—S—S—$R^2$, unsubstituted and substituted thiophenes, and combinations thereof; and the at least one co-solvent is a Lewis base co-solvent selected from the group consisting of ethers, dialkyl sulfides, amines, mono- and polyhydric alcohols, and mixtures thereof.

12. The method of claim 11 where the co-solvent is selected from the group consisting of a mono- and polyhydric alcohols having from 1 to 8 carbon atoms.

13. The method of claim 11 where the borohydride salt is selected from the group consisting of:

at least one inorganic borohydride salts having the formula $M^1BH_4$ where $M^1$ is selected from the group consisting of Li, Na, and K, or having the formula $M^2(BH_4)_2$ where $M^2$ is selected from the group consisting of Mg, Ca, and Zn;

ammonium salts of borohydride having the formula $R^3_4N^+BH_4^-$, where $R^3$ are independently C1 to C4 or arylalkyl (benzyl), where the alkyl groups are C1 to C4; and combinations thereof.

* * * * *